United States Patent [19]

Erdei

[11] 3,975,950
[45] Aug. 24, 1976

[54] APPARATUS FOR TESTING MATERIAL STRENGTH

[76] Inventor: Karoly Erdei, 1470 Morton Place, Los Angeles, Calif. 90026

[22] Filed: Mar. 17, 1975

[21] Appl. No.: 559,219

[52] U.S. Cl. ............................... 73/94; 73/103
[51] Int. Cl.² ........................................ G01N 3/10
[58] Field of Search ..................... 73/94, 103, 93

[56] References Cited
UNITED STATES PATENTS

| | | | |
|---|---|---|---|
| 2,346,281 | 4/1944 | Templin | 73/94 |
| 2,864,253 | 12/1958 | Lenton | 73/94 |
| 3,797,303 | 3/1974 | Bascoul et al. | 73/94 |

*Primary Examiner*—Jerry W. Myracle
*Attorney, Agent, or Firm*—William P. Green

[57] ABSTRACT

A machine for testing the strength of a specimen of a selected material, including spaced platens between which the specimen is confined during application of force thereto, with lamina packs being provided between the platens and specimen for transmitting force therebetween, and with each lamina pack consisting of a plurality of plates having interengaging highly polished surfaces facilitating differential lateral expansion or contraction of the plates in a manner permitting free lateral expansion or contraction of the specimen surface contacted by the lamina pack, and thereby avoiding introduction of substantial restraint to such expansion or contraction by the platens.

20 Claims, 9 Drawing Figures

APPARATUS FOR TESTING MATERIAL STRENGTH

BACKGROUND OF THE INVENTION

This invention relates to improved apparatus for testing the strength of a specimen of a selected material, such as for example a particular rock, concrete, or the like, under compressive forces. Certain features of the invention have been shown in Disclosure Document No. 036455 filed Oct. 31, 1974 in the U.S. Patent Office.

Conventional machines for testing material strength under compression take the form of presses having a pair of spaced platens between which the specimen to be tested is placed, and which are adapted to be pressed toward one another and against the specimen with great force, by hydraulic piston and cylinder mechanisms or other actuating means. The stresses developed in the specimen during such compression are monitored by a strain gauge or other equipment, and the point of breakdown of the material is recorded, to thus obtain an indication of the capacity of the material to withstand forces of different intensities.

In a somewhat different type of test of material strength, the specimen may be confined between two such platens while force is applied to the specimen in a lateral direction, that is, transversely of a line extending between the platens. Such lateral force may be applied in conjunction with compressive movement of the first mentioned platens, or without such movement and with the specimen merely being confined between the platens. The lateral force may be applied by a hydraulic fluid, or by additional platens acting transversely against the specimen.

A major difficulty which has been encountered in prior material testing equipment of this general type has involved inaccuracies in test results caused by frictional forces which are developed between the platens and the surfaces of the test specimens which are engaged by the platens. More specifically, under the high compressive forces which are encountered between the platens and specimen, the friction between the engaged faces of the platen and specimen causes the platen to resist very substantially lateral or transverse expansion of the specimen at those engaged faces as the specimen is compressed. Similarly, if the overall forces applied to the specimen are primarily lateral, the frictional interengagement of the platens and specimen may resist lateral contraction of the specimen which would otherwise occur at the interengaging faces of the specimen and platens. The platens are normally formed of a material which will not deform as much as the specimen under test pressures, and which by friction tends to restrain the engaged surfaces of the specimen to only such very limited change in dimension as is experienced by the platen itself. This restraint offered by the platens to deformation of the specimen under load necessarily alters the stress distribution pattern within the specimen, and adversely affects the accuracy of the test results, usually by giving an indication of greater strength in the specimen than it actually has.

In an attempt to eliminate such resistance by the platen to deformation of the sample being tested, it has heretofore been proposed that a relatively soft material be interposed between the platen and specimen for transmission of the compressive forces therebetween. For example, rubber has been utilized between the platen and specimen, as have Teflon, paste, building boards, and other similar materials or combinations of materials. However, these substances have by virtue of their relatively soft characteristics tended to squeeze out of the spaces between the platens and the test specimen, and in so squeezing out have exerted expansive forces on the engaged surfaces of the specimen which tend to increase its lateral deformation and, again, substantially alter the response of the specimen to the applied load. The test results achieved in this way may be as inaccurate as those achieved when the platen directly engages the specimen, though the effect on the results is usually reversed by tending to cause development of unintended tensile stresses in the specimen, and earlier breakage under compression than should occur.

SUMMARY OF THE INVENTION

A major purpose of the present invention is to provide improved material testing equipment in which the above discussed deficiencies of prior equipment are overcome by eliminating the introduction of any substantial effect by the platens on the lateral expansion or contraction of the test specimen under load. That is, the present equipment avoids any substantial tendency for the platens by friction to either resist or enhance the distortion of the specimen at its surfaces through which force is applied to the specimen from the platens, so that the specimen at those surfaces and throughout its entire mass is left completely free for unrestrained response to the applied load forces in a manner dictated by and accurately indicative of only the structural characteristics of the specimen material itself.

To achieve these results, I provide between the specimen and a platen a lamina pack, consisting of a plurality of flat plates, one of which engages a surface of the specimen, and another of which engages the platen. Successive ones of these plates have highly polished relatively slidable surfaces which by virtue of their extremely smooth condition are capable of shifting slightly relative to one another under compressive forces. The plate which is in contact with the specimen can therefore expand or contract in correspondence with the contacted surface of the specimen without introduction of substantial restraint, while the plate which is in contact with the platen can follow essentially its pattern of very slight lateral expansion or contraction. The difference between the extents of expansion or contraction of these two specimen and platen contacted plates is compensated for by relative shifting movement of the plates at the discussed opposed highly polished smooth surfaces. For best results, the plates are desirably formed of a metal, optimally steel having characteristics similar to those of the platens, and preferably with the value of Poisson's ratio divided by the modulus of elasticity being approximately the same for the plates and platens.

BRIEF DESCRIPTION OF THE DRAWINGS

The above and other features and objects of the invention will be better understood from the following detailed description of the typical embodiments illustrated in the accompanying drawings, in which.

DESCRIPTION OF THE PREFERRED EMBODIMENTS

Figure 1:
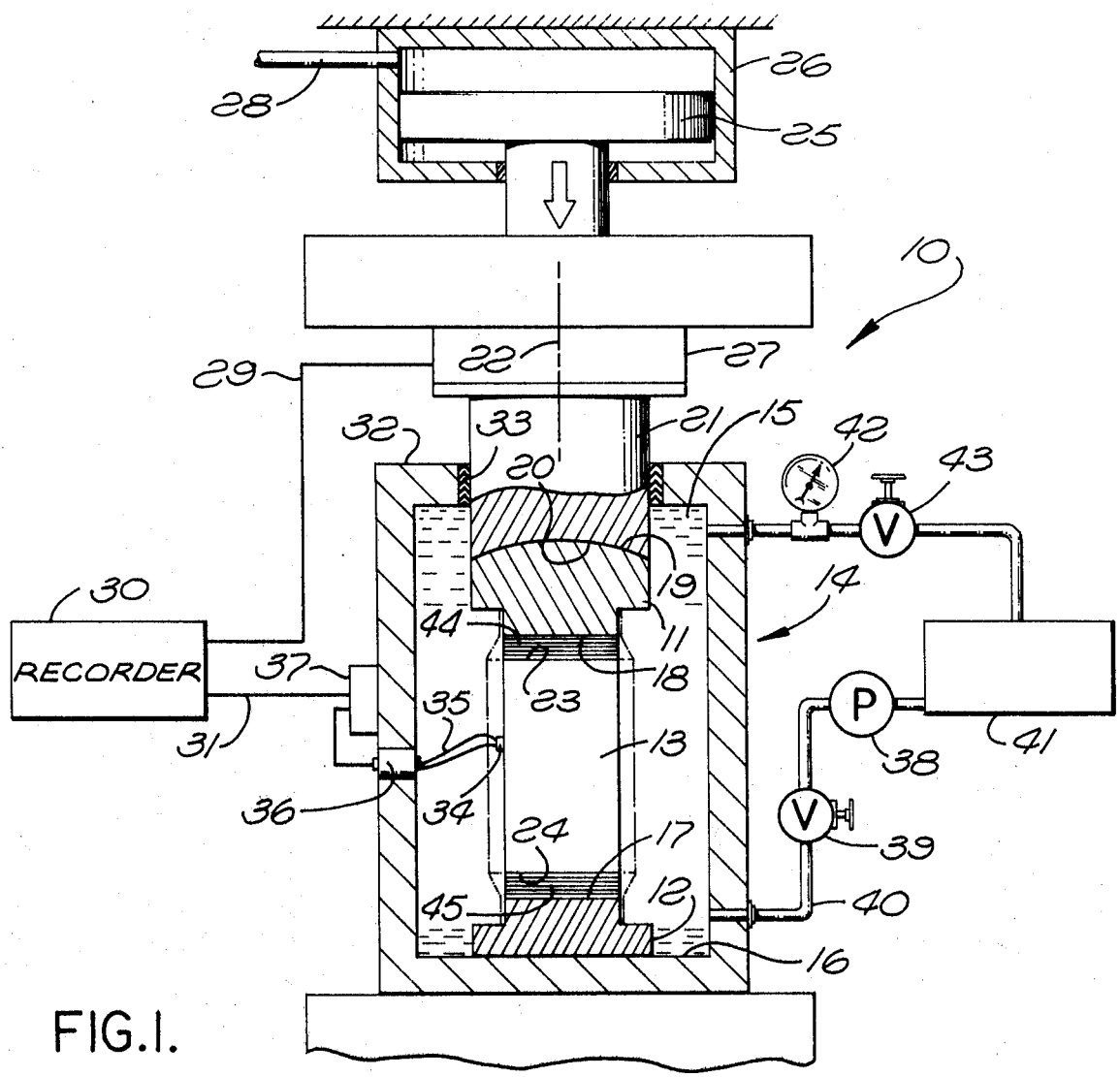
FIG. 1 is a vertical section through a material testing machine constructed in accordance with the invention, with some of the conventional portions of the machine illustrated somewhat diagrammatically.

Referring first to FIG. 1, there is illustrated at 10 a material strength testing machine including an upper movable platen 11 and a lower typically stationary platen 12 between which a specimen 13 of the material to be tested is received. The specimen and platens are contained within an outer fluid tight case 14 within which a body of liquid 15 is contained for applying lateral force to the specimen. The platens and case 14 are formed of a very strong rigid material, such as an appropriate steel of suitable thickness, capable of withstanding extremely high forces and pressures without substantial deformation during a testing operation.

The bottom platen 12 rests on and is secured in fixed position to and supported rigidly by a bottom wall 16 of case 14. The upper surface 17 of platen 12 through which vertical forces are transmitted to specimen 13 is desirably planar and essentially smooth and disposed precisely horizontally.

The upper platen 11 has an undersurface 18 which is planar and smooth and disposed precisely horizontal and parallel to upper surface 17 of the lower platen. In order to allow slight shifting movement of platen 11 into proper parallelism with respect to platen 12, the upper platen may have a spherical top surface 19 engaging a correspondingly spherically curved undersurface 20 of a ram element 21 which is movable vertically along axis 22 relative to the case and lower platen. Thus, platen 11 is free for slight universal movement about the center of spherical surfaces 19 and 20 relative to the ram 21, to bring surface 18 to an exactly horizontal position precisely parallel to surface 17, or if the upper and lower surfaces of specimen 13 are not exactly parallel to one another, to allow shifting movement of surface 18 into a slightly angular relation with respect to surface 17 corresponding to the angle between the upper and lower surfaces 23 and 24 of the specimen.

Ram 21 and platen 11 are actuable downwardly with great force by appropriate actuating means, which may include a piston 25 contained within a power cylinder 26 and acting through a load responsive cell 27 to move the ram and platen 11. Hydraulic actuating fluid is delivered to cylinder 26 above piston 25, as through an inlet line represented at 28. In lieu of the piston and cylinder mechanism 25–26, the specimen compressing force may be supplied in any other convenient manner, as for instance by a thermal jack in which heated rods force the platen downwardly, or by any other type of jack or press mechanism. A signal representing the force applied to the specimen through load cell 27 is delivered through an electrical conductor 29 to a recorder 30, to which there is delivered also another signal representing deformation of the specimen 13 through a conductor 31. The recorder 30 produces from these two signals a permanent printed record or other record indicating in graph form or otherwise the deformation of the specimen 13 at different compression forces.

Ram 21 may be appropriately sealed with respect to the top wall 32 of case 14 through which the ram extends, as by provision of annular chevron or other fluid seals represented diagrammatically at 33.

The deformation of specimen 13 may be sensed in any suitable manner, as by provision of a strain gauge 34 connected to the specimen at a convenient location and connected by conductors 35 through a sealed fluid tight plug 36 in the side wall of case 14 to a gauge 37 and the previously mentioned line 31 leading to the recorder. In some instances, a number of strain gauges may be provided at a number of different locations on the outer surface of specimen 13, to indicate and record its deformation at all of those different locations.

The specimen 13 is desirably of uniform horizontal section along its entire vertical extent, between its upper and lower horizontal top and bottom surfaces 23 and 24. This horizontal cross-section of the specimen may typically be the same as the horizontal cross-section of the engaged portions of the platens 11 and 12, and their horizontal surfaces 17 and 18. The horizontal cross-section of the specimen may typically be circular, square, rectangular, or any other selected sectional shape.

The pressurized liquid within space 15 in case 14 may be supplied by a high pressure pump 38 through a shut-off valve 39 in line 40, with the pump taking suction from a reservoir 41 to which liquid can be returned from the interior of the case past a pressure gauge 42 and a needle valve 43 which is adjustable to vary the pressure.

Figure 4:
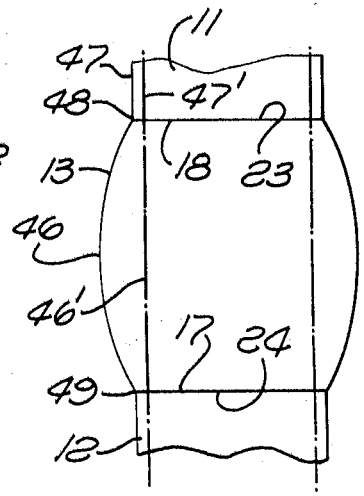
FIG. 4 is a view similar to FIG. 2, but showing the manner in which the specimen expands nonuniformly when compressed in conventional equipment without the use of the present lamina packs.

The portions of the FIG. 1 apparatus thus far described are conventional. The present invention is particularly concerned with the provision between the platens and specimen 13 of two lamina packs 44 and 45 for transmitting compressive forces from the platens to the specimen. FIG. 4 illustrates the manner in which specimen 13 deforms under compression if these lamina packs are not employed. Specifically, in that figure, the upper and lower surfaces 23 and 24 of specimen 13 are in direct engagement with surfaces 18 and 17 respectively of the platens. When compressive force is applied to the specimen by movement of upper platen 11 downwardly relative to lower platen 12, the vertically central portion of the specimen bulges laterally outwardly to a very substantial extent from the initial broken line position represented at 46' to the full line position 46. The platens 11 and 12, however, expand only very slightly between the broken line positions 47' and full line positions 47. Because of the frictional engagement between platen surfaces 17 and 18 and the specimen surfaces 24 and 23, the platen restrains the contacted surfaces of the specimen against substantial lateral expansion, and permits expansion at 48 and 49 only as much as the platens themselves can expand. The result is the illustrated non-uniform expansion and bulging effect, introducing non-uniform stresses into the specimen which are not actually characteristic of the specimen itself and do not reflect accurately the response which the specimen would have to compressive forces if there were no restraint resulting from contact with the platens.

As indicated previously, the lamina packs 44 and 45 of FIG. 1 are provided in order to prevent the non-uniform bulging of FIG. 4 when specimen 13 is vertically compressed. Each of the lamina packs includes a plurality of separately formed flat relatively thin plates 50 which may be identical with one another, and each of which has upper and lower planar, parallel horizontal surfaces 51 and 52 which are highly polished and extremely smooth to allow essentially unrestrained expansion of one plate relative to the next successive plate at their opposed polished surfaces. The coefficient of friction between the polished surfaces of each pair of successive plates is much less than the coefficient of friction between the various end plates of the two lamina packs and platen 11, platen 12, specimen surface 23, and specimen surface 24, and is also less than the coefficient of friction which would occur between the platens and the specimen if the lamina packs were omitted and the platens were allowed to contact the specimen directly. The opposed polished surfaces of successive plates may in some instances be entirely unlubricated and in direct contact with one another, or if desired may have a very thin preferably microscopic layer of a suitable oil or other lubricant therebetween.

In their undeformed state (full lines in FIG. 1), the plates may be of identical peripheral outline, corresponding to the circular, square, or other horizontal sectional configuration of the platens and specimen 13.

Plates 50 are formed of a material which is very hard and strong, and preferably have a hardness and strength approximately equaling the corresponding characteristics of platens 11 and 12. In most cases, the platens are formed of high strength steel, and plates 50 are similarly formed of a high strength steel capable of withstanding the high compressive forces encountered in use. It is contemplated, however, that in some instances other materials, such as other metals, may be utilized for the plates 50. For best results, the plates should be formed of a material for which the Poisson ratio divided by its modulus of elasticity (Young's modulus) is approximately equal to, and preferably substantially exactly equal to, the Poisson ratio for the platens divided by their modulus of elasticity. Each lamina pack includes at least two of the plates 50, and preferably at least four such plates with at least three pairs of opposed relatively slidably movable polished surfaces therebetween.

Figure 2:
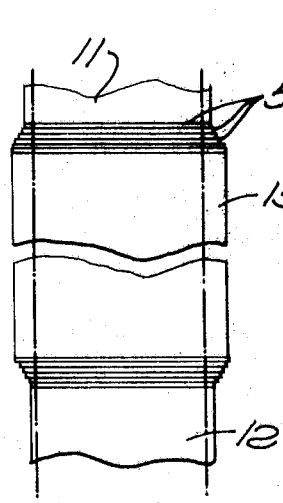
FIG. 2 is an enlarged fragmentary representation of the specimen, platens and lamina packs of the FIG. 1 arrangement.

In describing a cycle of use of the equipment of FIG. 1, assume that specimen 13 has been placed between the two platens 11 and 12, with the lamina packs 44 and 45 located as shown in FIG. 1. If the operator then delivers pressure fluid to cylinder 26, ram 21 and platen 11 are pressed downwardly relative to platen 12, to compress the specimen 13 of rock or other material vertically while causing its lateral expansion, as from the broken line condition of FIG. 2 to the full line condition of that figure. During such expansion, the engaging polished surfaces of successive plates in lamina packs 44 and 45 shift relative to one another in a manner allowing differential lateral expansion of the various plates. The two plates which directly contact the platens 11 and 12 are restrained by friction to a limited expansion corresponding substantially to that of the platens themselves, while the plates which contact the specimen directly expand substantially in correspondence with that specimen and offer little or no resistance to expansion of the contacted upper and lower surfaces of the specimen, so that the specimen can expand freely and with little or no restraint to the FIG. 2 uniform horizontal cross-section condition, rather than to the bulged condition of FIG. 4. The engaging polished surfaces of successive pairs of plates in the lamina packs move relative to one another just sufficiently to allow this relatively unrestrained and accurately characteristic expansion of the specimen.

Figure 3:
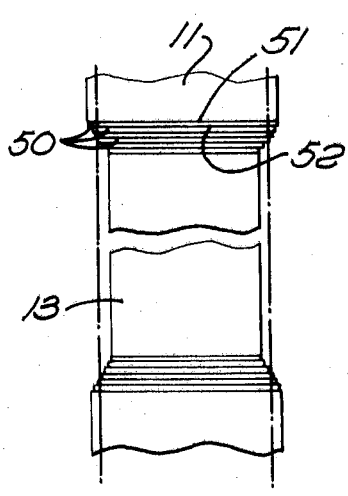
FIG. 3 is a view similar to FIG. 2, but showing the specimen and lamina packs under lateral compressive forces.

If pressure is developed within chamber 15 in case 14 during the application of vertical compressive force to the specimen by platens 11 and 12, the lateral or horizontal force exerted by the pressurized liquid against the specimen may resist its lateral expansion, or if the pressure is great enough to cause lateral contraction of the specimen as to the full line condition of FIG. 3. In some cases, this lateral pressure may be exerted against the specimen without moving the upper and lower platens 11 and 12 toward one another, but merely using them to confine the specimen during the lateral compression. In either event, when the specimen is compressed horizontally, the lamina packs 44 and 45 act in reverse to allow such horizontal contraction, again by virtue of the freely sliding engagement of the polished surfaces of successive plates in the lamina packs. The end plates which contact the platens contract only a slight amount corresponding to the slight contraction of the platens, and the plates which contact the specimen contract in correspondence with the engaged surfaces of the specimen without restraining such contraction.

Figure 5:
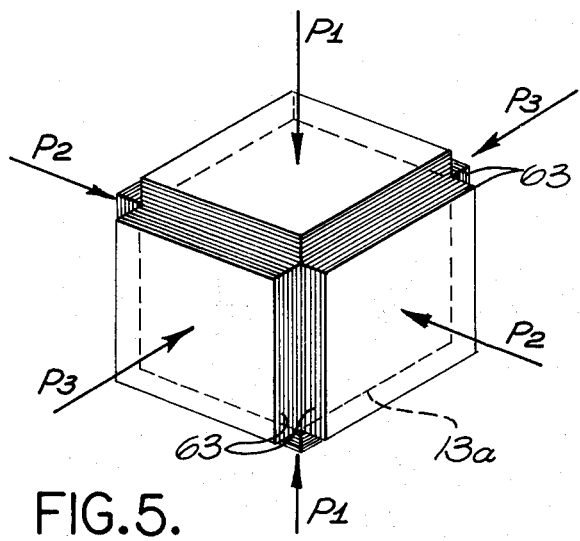
FIG. 5 represents diagrammatically the use of the present lamina packs in compressing a cubically shaped test specimen along three different mutually perpendicular axes.
Figure 6:
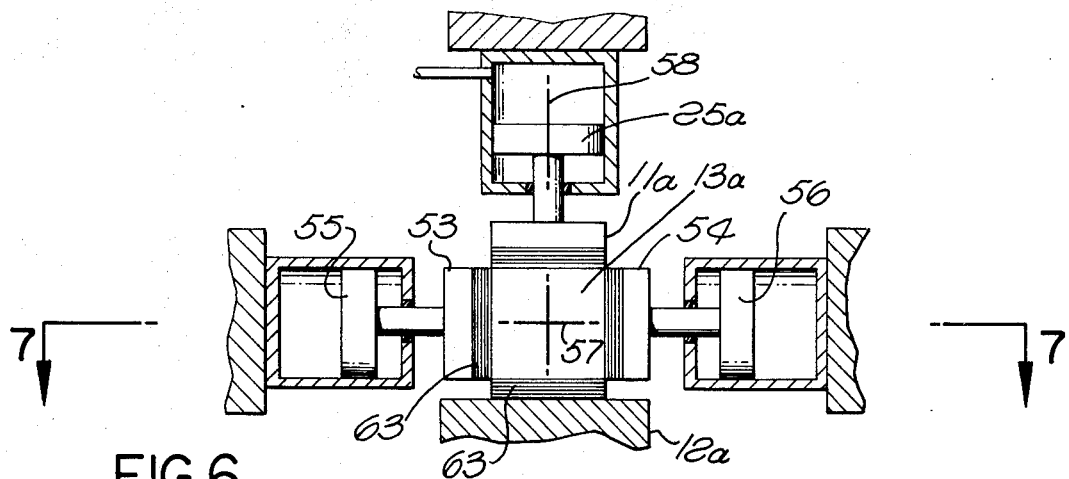
FIG. 6 is a central vertical section through a machine for performing a three axis compression test of the type represented diagrammatically in FIG. 5.
Figure 7:
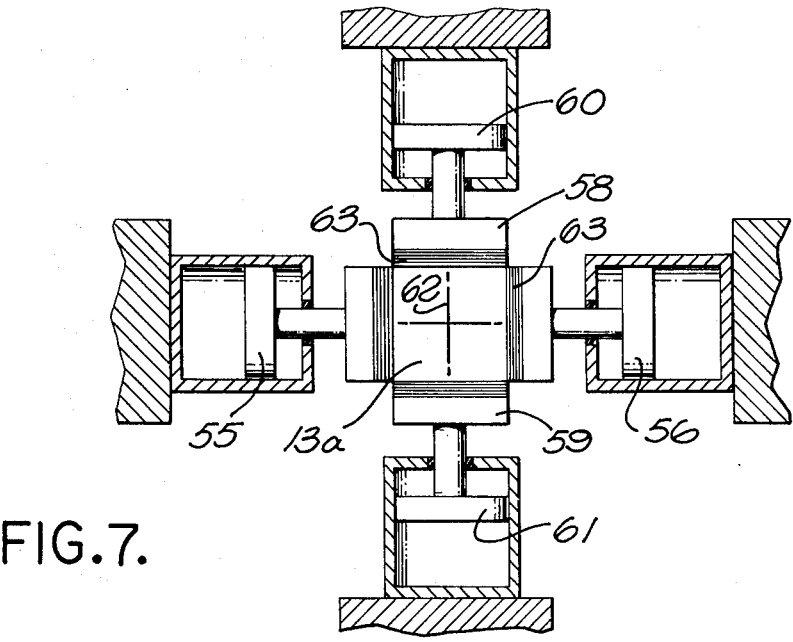
FIG. 7 is a horizontal section taken on line 7—7 of FIG. 6.

FIGS. 5 to 7 show a variational arrangement in which a typically cubically shaped specimen 13a is compressed in three different mutually perpendicular directions by three sets of platens. As seen in FIG. 6, a first pair of the platens 11a and 12a may be located above and beneath the specimen in correspondence with platens 11 and 12 of FIG. 1, with platen 11a being actuable downwardly with great force by fluid actuation of a piston 25a. Two additional opposed platens 53 and 54 actuated by a pair of fluid operated pistons 55 and 56 may compress the specimen in a first horizontal direction along a line represented at 57 perpendicular to the vertical line of action 58 of platens 11a and 12a. A second pair of opposed platens 58 and 59 actuated by hydraulic pistons 60 and 61 compress the specimen in a third direction represented by the horizontal line of action 62 of FIG. 7, which is perpendicular to both of the lines 57 and 58. Interposed between each of the platens 11a, 12a, 53, 54, 58 and 59 and the corresponding outer face of cubical specimen 13a is a lamina pack 63 corresponding to lamina packs 44 and 45 of the first form of the invention. Thus, upon compression of the specimen by the three pairs of platens with any possible combination of compressive forces in the three different directions, the polished plates of the various lamina packs allow free expansion and contraction of all of the six faces of cube 13a to whatever extent is dictated by the structural characteristics of the cube itself, without the changes in dimension of the cube being either resisted or enhanced by the platens and the lamina packs. The deformation of the cube can be read out by strain gauges or other means, in conjunction with readings of the various compressive forces to which the cube is subjected, to attain an accurate indication and record of the response of the material of the cube to those forces.

Figure 8:
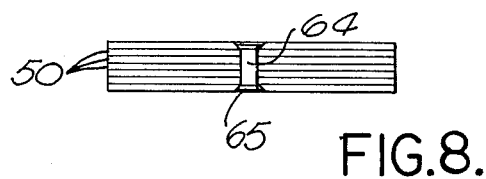
FIG. 8 shows a lamina pack utilizable in the present equipment and in which the plates of the pack are secured together for handling as a unit.

FIG. 8 shows a variational type of lamina pack which may be employed, and in which the various plates 50 may be exactly the same as described hereinabove, but with these plates being loosely connected together to facilitate handling by extension of a bolt or other connector 64 through aligned openings formed in the centers of the various plates. Bolt 64 may have enlarged heads 65 at its opposite ends for engaging upper and lower ones of the plates 50, with these heads being received within countersunk recesses in the top and bottom plates to avoid direct contact of the bolt with either a platen or a surface of the specimen being tested.

Figure 9:
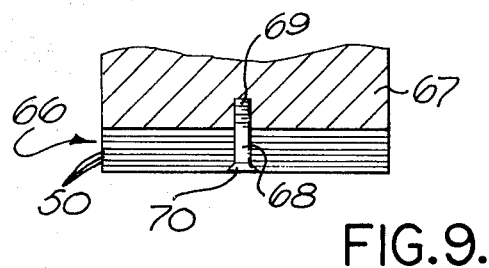
FIG. 9 shows a lamina pack in which the plates are secured loosely to the associated platen.

FIG. 9 shows another arrangement in which a lamina pack 66 formed of plates 50 identical with those previously described is secured loosely to a platen 67 by a bolt or other retainer 68, which may be threadedly connected into the platen at 69 and have an enlarged head 70 received within a countersunk recess in the lower one of the plates to retain all of the plates while avoiding direct contact of the bolt with a specimen being tested. The bolts 64 and 68 of FIGS. 8 and 9 thus retain the plates together but do not interfere with free relative movement of the engaging polished surfaces of the plates to attain the action discussed above.

While certain specific embodiments of the present invention have been disclosed as typical, the invention is of course not limited to these particular forms, but rather is applicable broadly to all such variations as fall within the scope of the appended claims.

I claim:

1. Apparatus for testing the strength of a specimen of material, comprising:
    two spaced platens between which said specimen is confined while force is applied to the specimen;
    a lamina pack interposed between a face of one of said platens and an opposed surface of said specimen for transmitting forces therebetween, said lamina pack including a plurality of plates one of which exerts force against said surface of the specimen and another of which is acted against by said platen face;
    successive ones of said plates having smooth opposed surfaces which are slidably movable laterally relative to one another under load in a relation permitting a change in lateral dimension of said surface of said specimen without substantial restraint being offered by said lamina pack; and
    means for monitoring the result when force is applied to said specimen while confined between said platens.

2. Apparatus as recited in claim 1, including means for applying force to said platens urging them relatively toward one another to compress said specimen therebetween.

3. Apparatus as recited in claim 1, including means for applying force to said specimen transversely of a line extending between said platens.

4. Apparatus as recited in claim 1, including a chamber for containing said specimen confined between said platens and with fluid received in the chamber about the specimen, and means for pressurizing said fluid to apply transverse force to the specimen.

5. Apparatus as recited in claim 1, including additional platens at opposite sides of said specimen for confining it in a direction disposed essentially transversely of the direction of confinement between said first mentioned platens, and an additional lamina pack between one of said additional platens and said specimen and including a plurality of additional plates one of which exerts force against said specimen and another of which is acted against by one of said additional platens, successive one of said additional plates having smooth opposed surfaces which are slidably movable relative to one another under load to allow relatively unrestrained change in dimension of the engaged surface of the specimen.

6. Apparatus as recited in claim 1, in which there is a second of said lamina packs between the second platen and said specimen and including a plurality of plates having opposed smooth relatively slidably movable surfaces.

7. Apparatus as recited in claim 1, in which said plates are formed of metal and said opposed relatively slidable surfaces thereof are highly polished.

8. Apparatus as recited in claim 1, in which said plates are formed of steel having highly polished surfaces.

9. Apparatus as recited in claim 1, in which said plates have a strength greater than that of said specimen and approximately the same as the strength of said platens.

10. Apparatus as recited in claim 1, in which said lamina pack includes at least four plates with at least three pairs of engaging smooth surfaces therebetween.

11. Apparatus as recited in claim 1, in which Poisson's ratio divided by the elastic modulus is approximately the same for said plates as for the engaged platen.

12. Apparatus as recited in claim 1, including means securing said plates together for handling while allowing relative lateral displacement thereof at said smooth opposed surfaces.

13. Apparatus as recited in claim 1, including a retaining element extending axially through said plates at a predetermined location and securing them together while allowing relative lateral displacement thereof.

14. Apparatus as recited in claim 1, including a retaining element extending through said plates and connected to said one platen and securing said plates to the platen while allowing relative lateral displacement of the plates.

15. Apparatus as recited in claim 1, in which said smooth opposed surfaces of said plates have a coefficient of friction less than that between an end one of said plates and said specimen.

16. Apparatus as recited in claim 1, in which said smooth opposed surfaces of said plates have a coefficient of friction less than either said platen or said specimen and an opposed one of the plates.

17. Apparatus as recited in claim 1, in which said smooth opposed surfaces of said plates have a coefficient of friction less than the coefficient of friction which would occur between said one platen and said specimen if they were allowed to contact directly and said lamina pack were omitted.

18. Apparatus as recited in claim 1, in which said monitoring means include means for indicating the load applied to said specimen by said platens, and means for indicating the amount of deformation of the specimen under load.

19. Apparatus for testing the strength of a specimen of material, comprising:
   two spaced platens between which said specimen is confined while force is applied to the specimen;
   a lamina pack interposed between a face of one of said platens and an opposed surface of said specimen for transmitting forces therebetween, said lamina pack including a plurality of plates one of which exerts force against said surface of the specimen and another of which is acted against by said platen face;
   successive ones of said plates having smooth opposed surfaces which are slidably movable laterally relative to one another under load in a relation permitting a change in lateral dimension of said surface of said specimen without substantial restraint being offered by said lamina pack;
   means for applying force to said platens urging them relatively axially together to compress said specimen;
   a second lamina pack between the second of said platens and the specimen and including a plurality of plates with smooth opposed highly polished surfaces;
   said plates of both lamina packs being formed of material for which the value of Poisson's ratio divided by the elastic modulus is approximately the same as for the platens; and
   means for indicating the load applied to the specimen by said platens; and
   means for indicating the stress developed in the specimen by said load.

20. Apparatus as recited in claim 19, including two additional pairs of opposed platens power actuable to compress said specimen along two mutually perpendicular axes both of which are perpendicular to the axis of compression of said first platens, there being four additional lamina packs between said four last mentioned platens respectively and the specimen and each including a plurality of plates having smooth highly polished planar surfaces.

* * * * *